US009205106B2

(12) United States Patent
Cool et al.

(10) Patent No.: US 9,205,106 B2
(45) Date of Patent: Dec. 8, 2015

(54) THERAPEUTIC BONE GROWTH AND REGENERATION

(75) Inventors: Simon McKenzie Cool, Singapore (SG); Victor Nurcombe, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 0 days.

(21) Appl. No.: 13/062,287

(22) PCT Filed: Sep. 7, 2009

(86) PCT No.: PCT/SG2009/000317
§ 371 (c)(1),
(2), (4) Date: Mar. 4, 2011

(87) PCT Pub. No.: WO2010/030241
PCT Pub. Date: Mar. 18, 2010

(65) Prior Publication Data
US 2011/0165218 A1 Jul. 7, 2011

Related U.S. Application Data

(60) Provisional application No. 61/096,272, filed on Sep. 11, 2008.

(30) Foreign Application Priority Data

Sep. 11, 2008 (GB) .................................... 0816650.6

(51) Int. Cl.
| A61M 31/00 | (2006.01) |
| A61F 2/02 | (2006.01) |
| A61K 31/737 | (2006.01) |
| A61P 19/08 | (2006.01) |
| B05D 5/00 | (2006.01) |
| C08B 37/10 | (2006.01) |
| A61K 31/726 | (2006.01) |
| A61L 27/34 | (2006.01) |
| A61F 2/00 | (2006.01) |
| A61F 2/28 | (2006.01) |
| A61F 2/30 | (2006.01) |

(52) U.S. Cl.
CPC ............ *A61K 31/737* (2013.01); *A61K 31/726* (2013.01); *A61L 27/34* (2013.01); *A61F 2002/0086* (2013.01); *A61F 2002/2817* (2013.01); *A61F 2002/3093* (2013.01); *A61L 2430/02* (2013.01)

(58) Field of Classification Search
CPC .... A61K 31/726; A61K 31/737; A61L 27/34; A61L 2430/02; C08L 5/10; A61F 2002/0086; A61F 2002/2817; A61F 2002/3093
USPC ........................................................ 424/423
See application file for complete search history.

(56) References Cited

U.S. PATENT DOCUMENTS

2005/0288252 A1* 12/2005 Nurcombe et al. ............. 514/56

FOREIGN PATENT DOCUMENTS

EP 1216718 6/2002
WO WO 96/02259 2/1996
WO WO 00/78356 12/2000
WO WO 2004/069298 8/2004
WO WO 2004/072100 8/2004
WO WO 2004/104188 12/2004
WO WO 2005/107772 11/2005
WO WO 2006/078211 7/2006
WO WO 2006/085209 8/2006

OTHER PUBLICATIONS

International Preliminary Report on Patentability mailed Mar. 24, 2011 in PCT/SG2009/000317.
European Patent Office Search Report issued on Mar. 22, 2012 in PCT/SG2009/000317.
Brickman et al. (1998) "Structural comparison of fibroblast growth factor-specific heparan sulfates derived from a growing differentiating neuroepithlial cell line", Glycobiology, vol. 8, No. 5, pp. 463-471.
Brickman et al. (Feb. 20, 1998) "Structural Modification of Fibroblast Growth Factor-binding Heparan Sulfate at a Determinative Stage of Neural Development", The Journal of Biological Chemistry, vol. 273, vo. 8, pp. 4350-4359.
Coombe & Kett, (2005) "Heparan sulfate-protein interactions; therapeutic potential through structure-function insights", Cellular and Molecular Life Sciences, vol. 62 pp. 410-424.
Ford-Perriss et al. (2002) "Variant heparan sulfates synthesized in developing mouse brain differentially regulate FGF signaling", Glycobiology, vol. 12, No. 11, pp. 721-727.
International Search Report and Written Opinion issued in PCT/SG2009/000317 on Oct. 21, 2009.
Jackson et al. (Apr. 2006) "The Use of Heparan Sulfate to Augment Fracture Repair in a Rat Fracture Model", Journal of Orthopaedic Research, pp. 1-9.
Jackson et al. (2007) "Heparan Sulfate Regulates the Anabolic Activity of MC3T3-E1 Preosteoblast Cells by Induction of Runx2", Journal of Cellular Physiology, vol. 210, pp. 38-50.
Luong-Van et al. (2007) "In vitro biocompatibility and bioactivity of microencapsulated heparan sulfate", Biomaterials, vol. 28, pp. 2127-2136.
Manton et al. (2007) "Disruption of Heparan and Chondroitin Sulfate Signaling Enhances Mesenchymal Stem Cell-Derived Osteogenic Differentiation via Bone Morphogenetic Protein Signaling Pathways", Stem Cells, vol. 25, pp. 2845-2854.
Nurcombe et al. (2007) "Temporal and functional changes in glycosaminoglycan expression during osteogenesis", J. Mol. Hist, vol. 38, pp. 469-481.
Taylor et al. (1994) FGF-2 Induces Regeneration of the Chick Limb Bud, Developmental Biology, vol. 163, pp. 282-284.
Woodruff et al. (2007) "Sustained release and osteogenic potential of heparan sulfate-doped fibrin glue scaffolds within rat cranial model", J. Mol. Hist, vol. 35, pp. 425-433.
Czekanska et al. "In Search of an Osteoblast Cell Model for In Vitro Research", European Cells and Materials, vol. 24, pp. 1-17 (2012).

* cited by examiner

*Primary Examiner* — Anoop Singh
*Assistant Examiner* — Doan Phan
(74) *Attorney, Agent, or Firm* — Swanson & Bratschun, L.L.C.

(57) ABSTRACT

The use of Herapan Sulphate 2 (HS-2) in therapeutic bone growth and regeneration is described. Herapan Sulphate 2 was identified as a variant of Heparan Sulphate purified from embryonic day (E10) of murine neuroepithelia.

7 Claims, 8 Drawing Sheets

| CONDITION | E 10 |
|---|---|
| pronase | 40,000 |
| mild alkali treatment | 25,000 |
| heparinase | 7,000 |
| number of heparinase resistant domains | 2 |

Figure 9

| | % E10 |
|---|---|
| TREATMENT | |
| Heparitinase | 61.5 |
| Heparinase | 15.3 |
| $HNO_2$ | 49.0 |

Figure 10

|  | %E10 GAG |
|---|---|
| DISACCHARIDE |  |
| IdoA/GlcA-AMann$_R$ | 12.9 |
| IdoA(2S)-AMann$_R$ | 53.4 |
| GlcA-AMann$_R$(6S) | 10.25 |
| IdoA-AMann$_R$(6S) | 3.4 |
| IdoA(2S)-AMann$_R$(6S) | 18.7 |
| GlcA(2S)-AMann$_R$ | 1.0 |
| GlcA-AMann$_R$(3S) | 0.30 |
| GlcA- AMann$_R$(3,6S) | 0.15 |
| UNKNOWN | 0.0 |

Figure 11

|  | % IN E10 |
|---|---|
| sulfation number : peak number |  |
| Non-sulfated : 1 | 37.2 |
| Mono-sulfated : 1 | 1.5 |
| Mono-sulfated : 2 | 1.0 |
| Mono-sulfated : 3 | 0.3 |
| Mono-sulfated : 4 | 0.3 |
| Mono-sulfated : 5 | 7.7 |
| Mono-sulfated : 6 | 23.9 |
| Mono-sulfated : 7 | 18.4 |
| Mono-sulfated : 8 | 0.7 |
| Mono-sulfated : 9 | 0.4 |
| Di-sulfated : 1 | 1.8 |
| Di-sulfated : 2 | 0.9 |
| Di-sulfated : 3 | 2.7 |
| Di-sulfated : 4 | 1.5 |
| Tri-sulfated : 1 | 1.0 |
| Tri-sulfated : 2 | 0.0 |
| Tri-sulfated : 3 | 0.3 |
| Tri-sulfated : 4 | 0.4 |
| TOTAL | 100 |

Figure 12

| PEAK NUMBER | DISACCHARIDE | % in E10 GAG |
|---|---|---|
| 1 | ΔHexUA-GlcNAc | 44.8 |
| 3 | ΔHexUA-GlcNSO$_3$ | 21.5 |
| 2 | ΔHexUA-GlcNAc(6S) | 8.0 |
| 7 | ΔHexUA(2S)-GlcNAc | 2.4 |
| 4 | ΔHexUA-GlcNSO$_3$(6S) | 4.0 |
| 5 | ΔHexUA(2S)-GlcNSO$_3$ | 12.4 |
| 8 | ΔHexUA(2S)-GlcNAc(6S) | 0.2 |
| 6 | ΔHexUA(2S)-GlcNSO$_3$(6S) | 4.1 |
| 9 | unknown | 2.4 |

Figure 13

| SULFATION | % in E10 GAG |
|---|---|
| Total sulfation/100 disaccharides | 77.4 |
| 6-O-Sulfate | 16.3 |
| 2-O-Sulfate | 19.1 |
| N-Sulfate | 42.0 |
| O-Sulfate | 35.4 |
| ratios of sulfations | |
| 2-O-Sulfate/6-O-Sulfate | 1.17 |
| N-Sulfate/O-Sulfate | 1.19 |
| N-Sulfate/2-O-Sulfate | 2.2 |
| N-Sulfate/6-Sulfate | 2.58 |

Figure 14

THERAPEUTIC BONE GROWTH AND REGENERATION

RELATED APPLICATIONS

This application is a 35 U.S.C. §371 national phase application of PCT/SG2009/000317, filed Sep. 7, 2009 (WO 2010/030241), entitled "Therapeutic Bone Growth and Regeneration." PCT/SG2009/000317 claims priority to U.S. Provisional Application Ser. No. 61/096,272, filed Sep. 11, 2008 and United Kingdom Application Serial No. 0816650.6, filed Sep. 11, 2008. Each of these applications is incorporated herein by reference in its entirety.

FIELD OF THE INVENTION

The present invention relates to the therapeutic growth and regeneration of bone tissue and particularly to the use of Heparan-Sulphate 2 in the therapeutic growth and regeneration of bone tissue.

BACKGROUND TO THE INVENTION

The drive to develop bone regenerative therapies to circumvent delayed and non-union of bone fractures is an important therapeutic issue, especially considering the millions of fractures which occur annually, at least 10% of which are unable to heal by themselves. Several growth factors play key roles in the process of bone repair, and studies aimed at elucidating the factors affecting stem cell fate have recently demonstrated that the extracellular glycosaminoglycan sugar heparan sulfate (HS) plays a key role in the proliferation and differentiation of human bone marrow-derived mesenchymal stem cells (1). Osteogenic lineage fate decisions in general are known to be strongly influenced by several heparan-binding growth factors and it is widely accepted that fibroblast growth factors (FGFs) and their receptors (FGFRs) are essential to osteoblast differentiation and proliferation (2-4). Much evidence has accumulated to show that FGF cognate binding to its receptor, and thus its intracellular signaling, as is the case with a large number of other growth and adhesive factors, is in fact controlled by HS (5).

Heparan sulfate is a member of the glycosaminoglycan family of macromolecules, linear polysaccharides consisting of a repeating glucosamine/glucuronic acid disaccharide unit backbone attached to a protein core. HS has highly but variably sulfated sequences contained within its chains, organized into clusters that subtend protein binding. These sulfated structural domain motifs are primarily responsible for the regulatory properties of HS (6). HS polysaccharides display versatilities in conformation and orientation of functional groups which enable them to employ different modes of binding with any individual protein or protein complex. These selective interactions with certain proteins thus result regulation of protein activities (7). HS thus acts as a co-receptor, binding to heparin-binding growth factors such as FGF and BMP2, both protecting them from proteolytic degradation and promoting binding to their high affinity receptors (7). HS has a low affinity yet high capacity for its ligands, so drawing them onto the cell surface and their high-affinity, cognate receptors which then transduce the appropriate signal into the cells (8). Moreover, HS binding is thought to be important in providing a matrix-bound pericellular reservoir of growth factors, so promoting their long-term availability to cells (9). BMPs are also thought to be brought into register by HS with their threonine-serine kinase BMP receptors (10-12).

HS derived from bone has been shown to improve bone regeneration when added exogenously in long bone healing (13). Jackson et al. (13) applied a single dose of bone-derived HS to a rat femoral fracture at the time of injury and showed an increase in callus size and bone volume after 2 weeks. Notably, these studies used single applications of HS derived from the MC3T3-E1 preosteoblast cell line in short-term delivery devices with promising results on the early stages of healing, but triggered little difference in the later stages.

Due to the temporal pattern of growth factor expression during bone repair, studies such as Luong Van et al (16) have looked into prolonging localized delivery of HS over longer periods of healing via the sustained release of HS from polycaprolactone microcapsules.

Fibrin glue enjoys widespread clinical application as a wound sealant, a reservoir to deliver growth factors and as an aid in the placement and securing of biological implants (19-22). Several studies have shown that fibrin glue promotes the regrowth of peripheral nerves to levels comparable with standard microsurgery, making it a popular candidate for experimental nerve repair (17). In the cellular environment, fibrin specifically binds to a variety of proteins, including fibronectin, albumin, FGF2, VEGF, and IL-1 (18). These properties make it an interesting drug and cell delivery system for various applications in tissue engineering (19-23). In each case tissue regenerative capabilities were investigated with respect to tailoring the scaffold to generate certain release profiles of the growth factors over time.

Heparan Sulphate 2 was identified and described in Brickman et al. (1998), J. Biol. Chem. 273(8), 4350-4359) and was purified from embryonic day 10 (E10) murine-neuroepithelia.

SUMMARY OF THE INVENTION

In a first aspect of the present invention HS-2 is provided for use in a method of medical treatment. In particular, HS-2 is provided for use in a method of treating bone fracture.

Pharmaceutical compositions and medicaments comprising HS-2 are provided. In one aspect of the present invention pharmaceutical compositions and medicaments comprising HS-2 are provided for use in a method of treatment, the method comprising treatment of bone fracture.

In a further aspect of the present invention a biocompatible implant or prosthesis comprising a biomaterial and HS-2 is provided. The implant or prosthesis is preferably for use in a method of treating bone fracture. The implant or prosthesis is preferably coated or impregnated with HS-2.

In another aspect of the present invention the use of HS-2 in the manufacture of a medicament for the treatment of bone fracture is provided. The medicament may comprise a biocompatible implant or prosthesis comprising a biomaterial and HS-2, as described herein. In another aspect of the present invention a method of forming a biocompatible implant or prosthesis is provided, the method comprising the step of coating or impregnating a biomaterial with HS-2.

In a further aspect of the present invention a method of treating a bone fracture in a subject is provided, the method comprising administration of a therapeutically effective amount of HS-2 to the subject. The method may comprise administering HS-2 to the tissue surrounding the fracture. The method may comprise injection of HS-2 to the tissue surrounding the fracture.

In a further aspect of the present invention a method of treating bone fracture in a subject is provided, the method comprising surgically implanting a biocompatible implant or prosthesis, which implant or prosthesis comprises a biomaterial and HS-2, into tissue of the subject at or surrounding the site of fracture.

In the present invention HS-2 may be formulated as a pharmaceutical composition or medicament comprising HS-2, optionally comprising a pharmaceutically acceptable carrier, adjuvant or diluent. It may also comprise of bioactive fragments derived from, or analogues to, the parent HS-2 molecule.

In yet a further aspect of the present invention a method of stimulating the growth or regeneration of bone tissue in a subject in vivo is provided comprising administering HS-2 to bone tissue in need of such stimulation.

DESCRIPTION OF PREFERRED EMBODIMENTS

The present invention is concerned with the therapeutic use (human and veterinary) of HS-2 to treat bone fracture. HS-2 is reported here to augment wound healing in bone. HS-2 stimulates bone regeneration in response to injury and contributes to improved wound healing in bone. HS-2 provides improvements in the speed of bone fracture repair enabling a reduction in the recovery time from injury.

Bone fracture is a medical condition. In this application "fracture" includes damage or injury to bone in which a bone is cracked, broken or chipped. A break refers to discontinuity in the bone. A fracture may be caused by physical impact, or mechanical stress or by medical conditions such as osteoporosis or osteoarthritis.

Orthopedic classification of fractures includes closed or open and simple or multi-fragmentary fractures. In closed fractures the skin remains intact, whilst in an open fracture the bone may be exposed through the wound site, which brings a higher risk of infection. Simple fractures occur along a single line, tending to divide the bone in two. Multi-fragmentary fractures spilt the bone into multiple pieces.

Other fracture types include, compression fracture, compacted fracture, spiral fracture, complete and incomplete fractures, transverse, linear and oblique fractures and comminuted fractures.

In most subjects bone healing (fracture union) occurs naturally and is initiated following injury. Bleeding normally leads to clotting and attraction of white blood cells and fibroblasts, followed by production of collagen fibres. This is followed by bone matrix (calcium hydroxyapatite) deposition (mineralisation) transforming the collagen matrix into bone. Immature re-generated bone is typically weaker than mature bone and over time the immature bone undergoes a process of remodelling to produce mature "lamellar" bone. The complete bone healing process takes considerable time, typically many months.

Bones in which fractures occur and which may benefit from treatment using HS-2 include all bone types, particularly all mammalian bones including, but not limited to, long bones (e.g. femur, humerus, phalanges), short bones (e.g. carpals, tarsals), flat bones (e.g. cranium, ribs, scapula, sternum, pelvic girdle), irregular bones (e.g. vertebrae), sesamoid bones (e.g. patella).

Bone fracture also includes pathological porosity, such as that exhibited by subjects with osteoporosis.

Although not limiting to the present invention, the primary actions of HS-2 may be on cells within, adjacent to, or caused to migrate into the wound site and may be on the bone stem cells, the preosteoblasts or the osteoblasts, or on any of the ancillary or vasculogenic cells found or caused to migrate into or within the wound bed.

HS-2 and pharmaceutical compositions and medicaments comprising HS-2 are provided for use in a method of treatment of bone fracture in a mammalian subject.

HS-2 may be purified and isolated as described in Brickman et al. (1998), *J. Biol. Chem.* 273(8), 4350-4359.

Treatment may comprise wound healing in bone. The treatment may involve repair, regeneration and growth of bone. HS-2 facilitates fracture repair by facilitating new bone growth. HS-2 acts to improve the speed of fracture repair enabling bone healing to occur faster leading to improved recovery time from injury. Treatment may lead to improved bone strength.

Treatment may also include treatment of osteoporosis or osteoarthritis.

Administration of HS-2 is preferably to the tissue surrounding the fracture. This may include administration directly to bone tissue in which the fracture has occurred. Administration may be to connective tissue surrounding the bone or fracture or to vasculature (e.g. blood vessels) near to and supplying the bone. Administration may be directly to the site of injury and may be to a callus formed by initial healing of the wound.

Medicaments and pharmaceutical compositions according to the present invention may be formulated for administration by a number of routes. Most preferably HS-2 is formulated in fluid or liquid form for injection.

Administration is preferably in a "therapeutically effective amount", this being sufficient to improve healing of the bone fracture compared to a corresponding untreated fracture. The actual amount administered, and rate and time-course of administration, will depend on the nature and severity of the fracture. Prescription of treatment, e.g. decisions on dosage etc, is within the responsibility of general practitioners and other medical doctors, and will typically take account of the nature of the fracture, the condition of the individual patient, the site of delivery, the method of administration and other factors known to practitioners. Single or multiple administrations of HS-2 doses may be administered in accordance with the guidance of the prescribing medical practitioner. Purely by way of example, HS-2 may be delivered in dosages of at least 1 ng/ml, more preferably at least 5 ng/ml and optionally 10 ng/ml or more. Individual HS-2 dosages may be of the order less than 1 mg and greater than tug, e.g. one of about 5 µg, about 10 µg, about 25 µg, about 50 µg, about 100 µg, about 0.5 mg, or about 1 mg. Examples of the techniques and protocols mentioned above can be found in Remington's Pharmaceutical Sciences, 20th Edition, 2000, pub. Lippincott, Williams & Wilkins.

HS-2 may be used to treat bone fracture alongside other treatments, such as administration of pain relieving or anti-inflammatory medicaments, immobilisation and setting of the bone, e.g. immobilising the injured limb in a plaster cast, surgical intervention, e.g. to re-set a bone or move a bone to correct displacement, angulation or dislocation. If surgery is required HS-2 may be administered directly to (e.g. applied to) the fracture during the surgical procedure.

Pharmaceutical compositions and medicaments of the invention may take the form of a biomaterial that is coated and/or impregnated with HS-2. An implant or prosthesis may be formed from the biomaterial. Such implants or prostheses may be surgically implanted to assist in bone growth, regeneration, restructuring and/or re-modelling.

HS-2 may be applied to implants or prostheses to accelerate new bone formation at a desired location. It will be appreciated that heparan sulphates, unlike proteins, are particularly robust and have a much better ability to withstand the solvents required for the manufacture of synthetic bioscaffolds and application to implants and prostheses.

The biomaterial may be coated or impregnated with HS-2. Impregnation may comprise forming the biomaterial by mixing HS-2 with the constitutive components of the biomaterial, e.g. during polymerisation, or absorbing HS-2 into the biomaterial. Coating may comprise adsorbing the HS-2 onto the surface of the biomaterial.

The biomaterial should allow the coated or impregnated HS-2 to be released from the biomaterial when administered to or implanted in the subject. Biomaterial release kinetics may be altered by altering the structure, e.g. porosity, of the biomaterial.

In addition to coating or impregnating a biomaterial with HS-2, one or more biologically active molecules may be impregnated or coated on the biomaterial. For example, at least one chosen from the group consisting of: BMP-2, BMP-4, OP-1, FGF-1, FGF-2, TGF-β1, TGF-β2, TGF-β3; VEGF; collagen; laminin; fibronectin; vitronectin. In addition or alternatively to the above bioactive molecules, one or more bisphosphonates may be impregnated or coated onto the biomaterial along with HS-2. Examples of useful bisphosphonates may include at least one chosen from the group consisting of: etidronate; clodronate; alendronate; pamidronate; risedronate; zoledronate.

Biomaterials coated or impregnated with HS-2 may be useful in both medical and veterinary purposes. It will be appreciated that the present invention may improve the quality of life of a patient or potentially extend the life of an animal, for example a valuable race horse for use in breeding.

The biomaterial provides a scaffold or matrix support. The biomaterial may be suitable for implantation in tissue, or may be suitable for administration (e.g. as microcapsules in solution).

The implant or prosthesis should be biocompatible, e.g. non-toxic and of low immunogenicity (most preferably non-immunogenic). The biomaterial may be biodegradable such that the biomaterial degrades as wound healing occurs, ultimately leaving only the regenerated bone in situ in the subject. Alternatively a non-biodegradable biomaterial may be used, e.g. to guide bone regeneration over a large discontinuity and/or to act as a structural support during bone healing, with surgical removal of the biomaterial being an optional requirement after successful wound healing.

Biomaterials may be soft and/or flexible, e.g. hydrogels, fibrin web or mesh, or collagen sponges. A "hydrogel" is a substance formed when an organic polymer, which can be natural or synthetic, is set or solidified to create a three-dimensional open-lattice structure that entraps molecules of water or other solutions to form a gel. Solidification can occur by aggregation, coagulation, hydrophobic interactions or cross-linking.

Alternatively biomaterials may be relatively rigid structures, e.g. formed from solid materials such as plastics or biologically inert metals such as titanium.

The biomaterial may have a porous matrix structure which may be provided by a cross-linked polymer. The matrix is preferably permeable to nutrients and growth factors required for bone growth.

Matrix structures may be formed by by crosslinking fibres, e.g. fibrin or collagen, or of liquid films of sodium alginate, chitosan, or other polysaccharides with suitable crosslinkers, e.g. calcium salts, polyacrylic acid, heparin. Alternatively scaffolds may be formed as a gel, fabricated by collagen or alginates, crosslinked using well established methods known to those skilled in the art.

Suitable polymer materials for matrix formation include, but are not limited by, biodegradable/bioresorbable polymers which may be chosen from the group of: collagen, fibrin, chitosan, polycaprolactone, poly(DL-lactide-co-caprolactone), polyp lactide-co-caprolactone-co-glycolide), polyglycolide, polylactide, polyhydroxyalcanoates, co-polymers thereof, or non-biodegradable polymers which may be chosen from the group of: cellulose acetate; cellulose butyrate, alginate, agarose, polysulfone, polyurethane, polyacrylonitrile, sulfonated polysulfone, polyamide, polyacrylonitrile, polymethylmethacrylate, co-polymers thereof.

Collagen is a promising material for matrix construction owing to its biocompatibility and favourable property of supporting cell attachment and function (U.S. Pat. No. 5,019, 087; Tanaka, S.; Takigawa, T.; Ichihara, S. & Nakamura, T. Mechanical properties of the bioabsorbable polyglycolic acid-collagen nerve guide tube *Polymer Engineering & Science* 2006, 46, 1461-1467). Clinically acceptable collagen sponges are one example of a matrix and are well known in the art (e.g. from Integra Life Sciences).

Fibrin scaffolds (e.g. fibrin glue) provide an alternative matrix material.

Luong-Van et al (In vitro biocompatibility and bioactivity of microencapsulated heparan sulphate *Biomaterials* 28 (2007) 2127-2136), incorporated herein by reference, describes prolonged localised delivery of HS from polycaprolactone microcapsules.

A further example of a biomaterial is a polymer that incorporates hydroxyapatite or hyaluronic acid.

The biomaterial can be supplemented with additional cells. For example, one can "seed" the biomaterial (or co-synthesise it) with undifferentiated bone precursor cells, e.g. stem cells such as mesenchymal stem cells, more preferably human mesenchymal stem cells.

The subject to be treated may be any animal or human. The subject is preferably mammalian, more preferably human. The subject may be a non-human mammal (e.g. rabbit, guinea pig, rat, mouse or other rodent (including cells from any animal in the order Rodentia), cat, dog, pig, sheep, goat, cattle, horse, non-human primate), but is more preferably human. The subject may be male or female. The subject may be a patient.

Woodruff et al (Sustained release and osteogenic potential of heparan sulfate-doped fibrin glue scaffolds within a rat cranial model *J Mol Hist* (2007) 38:425-433) is hereby incorporated by reference in its entirety.

Heparan Sulphate

Heparan sulfate proteoglycans (HSPGs) represent a highly diverse subgroup of proteoglycans and are composed of heparan sulfate glycosaminoglycan side chains covalently attached to a protein backbone. The core protein can exist in three forms: a secreted form known as perlecan, a form anchored in the plasma membrane known as glypican, and a transmembrane form known as syndecan. They are ubiquitous constituents of mammalian cell surfaces and most extracellular matrices.

"Heparan Sulphate" ("Heparan sulfate" or "HS") is initially synthesised in the Golgi apparatus as polysaccharides consisting of tandem repeats of D-glucuronic acid (GlcA) and N-acetyl-D-glucosamine (GlcNAc). The nascent polysaccharides may be subsequently modified in a series of steps: N-deacetylation/N-sulfation of GlcNAc, C5 epimerisation of GlcA to iduronic acid (IdoA), O-sulphation at C2 of IdoA and GlcA, O-sulphation at C6 of N-sulphoglucosamine (GlcNS) and occasional O-sulphation at C3 of GlcNS. N-deacetylation/N-sulphation, 2-O-, 6-O- and 3-O-sulphation of HS are mediated by the specific action of HS N-deacetylase/N-sulfotransferase (HSNDST), HS 2-O-sulfotransferase (HS2ST), HS 6-O-sulfotransferase (HS6ST) and HS 3-O-sulfotransferase, respectively. At each of the modification steps, only a fraction of the potential substrates are modified, resulting in considerable sequence diversity. This structural complexity of HS has made it difficult to determine its sequence and to understand the relationship between HS structure and function.

Heparan sulfate side chains consist of alternately arranged D-glucuronic acid or L-iduronic acid and D-glucosamine, linked via (1→4) glycosidic bonds. The glucosamine is often N-acetylated or N-sulfated and both the uronic acid and the glucosamine may be additionally O-sulfated. The specificity of a particular HSPG for a particular binding partner is created by the specific pattern of carboxyl, acetyl and sulfate groups attached to the glucosamine and the uronic acid. In contrast to heparin, heparan sulfate contains less N- and O-sulfate groups and more N-acetyl groups. The heparan sulfate side chains are linked to a serine residue of the core protein through a tetrasaccharide linkage (-glucuronosyl-β-(1→3)-galactosyl-⊖-(1→3)-galactosyl-β-(1→4)-xylosyl-β-1-O-(Serine)) region.

Both heparan sulfate chains and core protein may undergo a series of modifications that may ultimately influence their biological activity. Complexity of HS has been considered to surpass that of nucleic acids (Lindahl et al, 1998, *J. Biol. Chem.* 273, 24979; Sugahara and Kitagawa, 2000, *Curr. Opin. Struct. Biol.* 10, 518). Variation in HS species arises from the synthesis of non-random, highly sulfated sequences of sugar residues which are separated by unsulfated regions of disaccharides containing N-acetylated glucosamine. The initial conversion of N-acetylglucosamine to N-sulfoglucosamine creates a focus for other modifications, including epimerization of glucuronic acid to iduronic acid and a complex pattern of O-sulfations on glucosamine or iduronic acids. In addition, within the non-modified, low sulfated, N-acetylated sequences, the hexuronate residues remain as glucuronate, whereas in the highly sulfated N-sulfated regions, the C-5 epimer iduronate predominates. This limits the number of potential disaccharide variants possible in any given chain but not the abundance of each. Most modifications occur in the N-sulfated domains, or directly adjacent to them, so that in the mature chain there are regions of high sulfation separated by domains of low sulfation (Brickman et al. (1998), *J. Biol. Chem.* 273(8), 4350-4359, which is herein incorporated by reference in its entirety).

It is hypothesized that the highly variable heparan sulfate chains play key roles in the modulation of the action of a large number of extracellular ligands, including regulation and presentation of growth and adhesion factors to the cell, via a complicated combination of autocrine, juxtacrine and paracrine feedback loops, so controlling intracellular signaling and thereby the differentiation of stem cells. For example, even though heparan sulfate glycosaminoglycans may be genetically described (Alberts et al. (1989) Garland Publishing, Inc, New York & London, pp. 804 and 805), heparan sulfate glycosaminoglycan species isolated from a single source may differ in biological activity. As shown in Brickman et al, 1998, *Glycobiology* 8, 463, two separate pools of heparan sulfate glycosaminoglycans obtained from neuroepithelial cells could specifically activate either FGF-1 or FGF-2, depending on mitogenic status. Similarly, the capability of a heparan sulfate (HS) to interact with either FGF-1 or FGF-2 is described in WO 96/23003. According to this patent application, a respective HS capable of interacting with FGF-1 is obtainable from murine cells at embryonic day from about 11 to about 13, whereas a HS capable of interacting with FGF-2 is obtainable at embryonic day from about 8 to about 10.

As stated above HS structure is highly complex and variable between HS. Indeed, the variation in HS structure is considered to play an important part in contributing toward the different activity of each HS in promoting cell growth and directing cell differentiation. The structural complexity is considered to surpass that of nucleic acids and although HS structure may be characterised as a sequence of repeating disaccharide units having specific and unique sulfation patterns at the present time no standard sequencing technique equivalent to those available for nucleic acid sequencing is available for determining HS sequence structure. In the absence of simple methods for determining a definitive HS sequence structure HS molecules are positively identified and structurally characterised by skilled workers in the field by a number of analytical techniques. These include one or a combination of disaccharide analysis, tetrasaccharide analysis, HPLC and molecular weight determination. These analytical techniques are well known to and used by those of skill in the art.

Two techniques for production of di- and tetra-saccharides from HS include nitrous acid digestion and lyase digestion. A description of one way of performing these digestion techniques is provided below, purely by way of example, such description not limiting the scope of the present invention.

Nitrous Acid Digestion

Nitrous acid based depolymerisation of heparan sulphate leads to the eventual degradation of the carbohydrate chain into its individual disaccharide components when taken to completion.

For example, nitrous acid may be prepared by chilling 250 μl of 0.5 M $H_2SO_4$ and 0.5 M $Ba(NO_2)_2$ separately on ice for 15 min. After cooling, the $Ba(NO_2)_2$ is combined with the $H_2SO_4$ and vortexed before being centrifuged to remove the barium sulphate precipitate. 125 μl of $HNO_2$ was added to GAG samples resuspended in 20 μl of $H_2O$, and vortexed before being incubated for 15 min at 25° C. with occasional mixing. After incubation, 1 M $Na_2CO_3$ was added to the sample to bring it to pH 6. Next, 100 μl of 0.25 M $NaBH_4$ in 0.1 M NaOH is added to the sample and the mixture heated to 50° C. for 20 min. The mixture is then cooled to 25° C. and acidified glacial acetic acid added to bring the sample to pH 3. The mixture is then neutralised with 10 M NaOH and the volume decreased by freeze drying. Final samples are run on a Bio-Gel P-2 column to separate di- and tetrasaccharides to verify the degree of degradation.

Lyase Digestion

Heparinise III cleaves sugar chains at glucuronidic linkages. The series of Heparinase enzymes (I, II and III) each display relatively specific activity by depolymerising certain heparan sulphate sequences at particular sulfation recognition sites. Heparinase I cleaves HS chains with NS regions along the HS chain. This leads to disruption of the sulphated domains. Heparinase III depolymerises HS with the NA domains, resulting in the separation of the carbohydrate chain into individual sulphated domains. Heparinase II primarily cleaves in the NA/NS "shoulder" domains of HS chains, where varying sulfation patterns are found. Note: The repeating disaccharide backbone of the heparan polymer is a uronic acid connected to the amino sugar glucosamine. "NS" means the amino sugar is carrying a sulfate on the amino group enabling sulfation of other groups at C2, C6 and C3. "NA" indicates that the amino group is not sulphated and remains acetylated.

For example, for depolymerisation in the NA regions using Heparinase III both enzyme and lyophilised HS samples are prepared in a buffer containing 20 mM Tris-HCL, 0.1 mg/ml BSA and 4 mM $CaCl_2$ at pH 7.5. Purely by way of example, Heparinase III may be added at 5 mU per 1 μg of HS and incubated at 37° C. for 16 h before stopping the reaction by heating to 70° C. for 5 min.

Di- and tetrasaccharides may be eluted by column chromatography.

In the present invention the heparan sulfate is heparan sulfate 2 (HS-2). HS-2 denominates the sugar chains of an HSPG, which have been found to have affinity for FGF-2. HS-2 has a molecular weight of approximately 25 kDa and thus, assuming an average molecular mass of 400 Da per disaccharide, consists of about 60 disaccharides. The disaccharide composition of HS-2 is set forth in Brickman et al. (Glycobiology Vo. 8 No. 5 pp. 463-471, 1998), which is herein incorporated by reference in its entirety.

By "heparan sulfate 2" or "HS-2" is meant the heparan sulfate that is described by Brickman et al. (1998), J. Biol. Chem. 273(8), 4350-4359) and that is derived (and obtainable) from embryonic neuroepitheffum, preferably mammalian embryonic neuroepithelium more preferably murine embryonic neuroepithelium, and is preferably capable of interacting with FGF-2. Accordingly, this heparan sulfate 2 is obtainable from heparan proteoglycans of murine cells at embryonic day 10 as described by Brickman (supra). The HS-2 that is used in the experimental section of the present application is derived from embryonic mouse, it has been found to be very potent on mouse, human, rat, chicken, Xenopus and drosophila cells. In line with these results a universal mechanism amongst any higher organism (for example insects or vertebrates such as mammals, birds, reptiles or fish) is contemplated here. Thus, any heparan sulfate 2 and any respective heparan sulfate proteoglycan that is capable of interacting with FGF-2 and that is able to promote or facilitate proliferation and/or maintenance of stem cells ex vivo (in vitro) is encompassed in the present invention, including such heparan sulfate proteoglycan and heparan sulfate 2 that is yet to be isolated from a specific species. The isolation and determination of the functionality of the isolated heparan sulfate or heparan sulfate proteoglycan is well within the knowledge of the person of ordinary skill in the art and can be carried out as described by Brickman et al. (1998), *J. Biol. Chem.* 273(8), 4350-4359, for example.

HS-2 can be obtained from embryonic day 10 (E10) mouse neuroepithelium. The molecular weight of HS-2 is shown in FIG. 9 following a variety of treatments including pronase treatment to remove any associated protein component, mild alkali and heparinase. HS-2 can be further characterised by analysis of the percentage of linkages sensitive to treatment with either low pH $HNO_2$, hepartinase or heparanase. The results are shown in FIG. 10. The disaccharide composition of HS-2 following nitrous acid digestion is shown in FIG. 11. The tetrasaccharide composition of HS-2 following nitrous acid digestion is shown in FIG. 12. The disaccharide composition of HS-2 following treatment with a mixture of heparin lyases is shown in FIG. 13. The sulfation characteristics of the disaccharides shown in FIG. 13 are shown in FIG. 14. Methodology for determining the percentage of linkages sensitive to susceptible treatment with either low pH $HNO_2$, heparitinase or heparanase; nitrous acid digestion and heparin lyase digestion are described elsewhere in this application.

In this specification reference to HS-2 includes HS obtained from embryonic day 10 (E10) mammalian neuroepithelturt preferably mouse. Reference to HS-2 may also include HS having substantially similar structure and/or function to HS-2 set forth in Brickman et al. in *Glycobiology* Vol. 8 No. 5 pp. 463-471, 1998. HS of substantial similarity to HS-2 of Brickman et at may include HS having:

(i) a molecular weight no more than 10%, more preferably 5%, greater or less than the molecular weight shown in FIG. 9 for the corresponding treatment; and/or (ii) a percentage of linkages susceptible to low pH nitrous acid, heparitinase or heparanase treatment that is no more than 10%, more preferably 5%, greater or less than the percentage shown in FIG. 10 for the corresponding treatment; and/or (iii) a nitrous acid digestion disaccharide composition wherein each disaccharide corresponding to those shown in FIG. 11 is present and the percentage composition of each disaccharide is no more than 20%, more preferably 15%, 10%, 5%, 3%, 2% or 1%, greater or less than the percentage composition shown in FIG. 11; and/or (iv) a nitrous acid digestion tetrasaccharide composition wherein each tetrasaccharide corresponding to those shown in FIG. 12 is present and the percentage composition of each tetrasaccharide is no more than 20%, more preferably no more than 15%, 10%, 5%, 3%, 2% or 1%, greater or less than the percentage composition shown in FIG. 12; and/or (v) a heparin lyase disaccharide composition wherein each disaccharide corresponding to those shown in FIG. 13 is present and the percentage composition of each disaccharide is no more than 20%, more preferably 15%, 10% or 5%, greater or less than the percentage composition shown in FIG. 13.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE FIGURES

Embodiments and experiments illustrating the principles of the invention will now be discussed with reference to the accompanying figures in which:

FIG. 9. A summary of the estimated $M_r$ of extracellular-HS2 from E10 neuroepithelium. The source of HS was subjected to separation on a 1×120 cm Sepharose CL-6B column after a variety of treatments. The size of purified full length HS was determined both before and after mild alkali treatment to determine the presence of more than one chain per protein core. In addition, the approximate distance between heparinase-sensitive disaccharides was determined by isolating the non-resolved, large oligosaccharides from a Bio-Gel P-10 column and rerunning them on a Sepharose CL-6B column.

FIG. 10. Proportion of the linkages in HS-2 susceptible to low pH $HNO_2$, heparitinase and heparinase. Radiolabelled heparan sulphate 2 was treated with low pH $HNO_2$, heparinase, or heparitinase and fractioned on a Bio-Gel P-10 column. The percentage of the total treatment-sensitive linkages was determined in two separate experiments by $\Sigma A_n/n$ where $A_n$ is the percentage of total radioactivity in that peak, and n is the number of disaccharide repeat units in the oligosaccharides as determined by the elution position (Turnbull and Gallagher, 1990; Kato et al. 1994).

FIG. 11. Nitrous acid-derived disaccharide composition of heparan sulfate from E10 neuroepithelia. Radiolabelled HS-2 was depolymerized by deaminitive cleavage with low pH $HNO_2$. Disaccharides were isolated after $HNO_2$ treatment of the GAGs and the samples then run on a 1×120 cm Bio-Gel P-2 column. The resulting disaccharides were fractionated by SAX-HPLC. Areas under the peaks were integrated to give therdisacchartde composition and subsequently, the percentage composition in each sample.

FIG. 12. Tetrasaccharides from $HNO_2$ treated HS-2 separated by SAX-HPLC. Tetrasaccharides derived from $HNO_2$ treated heparan sulfates were originally separated on a Bio-Gel P-2 column and were then further resolved on SAX-HPLC. The percentage of each was determined by calculating the radioactivity in each peak and comparing it to the total radioactivity in all peaks combined. Tetrasaccharide peak numbers in the left column correspond to the peaks from SAX-HPLC. The degree of sulfation was determined by comparison of these tritiated samples with peaks generated by dual $^{35}S/^3H$ radiolabelled samples (from Dr. Gordon Jayson, University of Manchester) run on the same column under identical conditions.

FIG. 13. Disaccharide composition of heparan sulfate from E10 neuroepithelium following heparin lyase treatment. Heparan sulfate 2 was completely depolymerized with a mixture of heparan lyases. The resulting unsaturated disaccharides were isolated on a P-2 column and fractionated by strong anion exchange column chromatography. The area under each resultant curve was integrated to calculate the percentage of each disaccharide in each sample. Numbers represent the average of two runs (for the primary GAG samples) and three runs (for the 2.3D derived samples). Over 97% disaccharides were recovered from each sample.

FIG. 14. Sulfation characteristics of disaccharides from the HS-2 pools shown in FIG. 13.

DETAILED DESCRIPTION OF THE INVENTION

Figure 1:
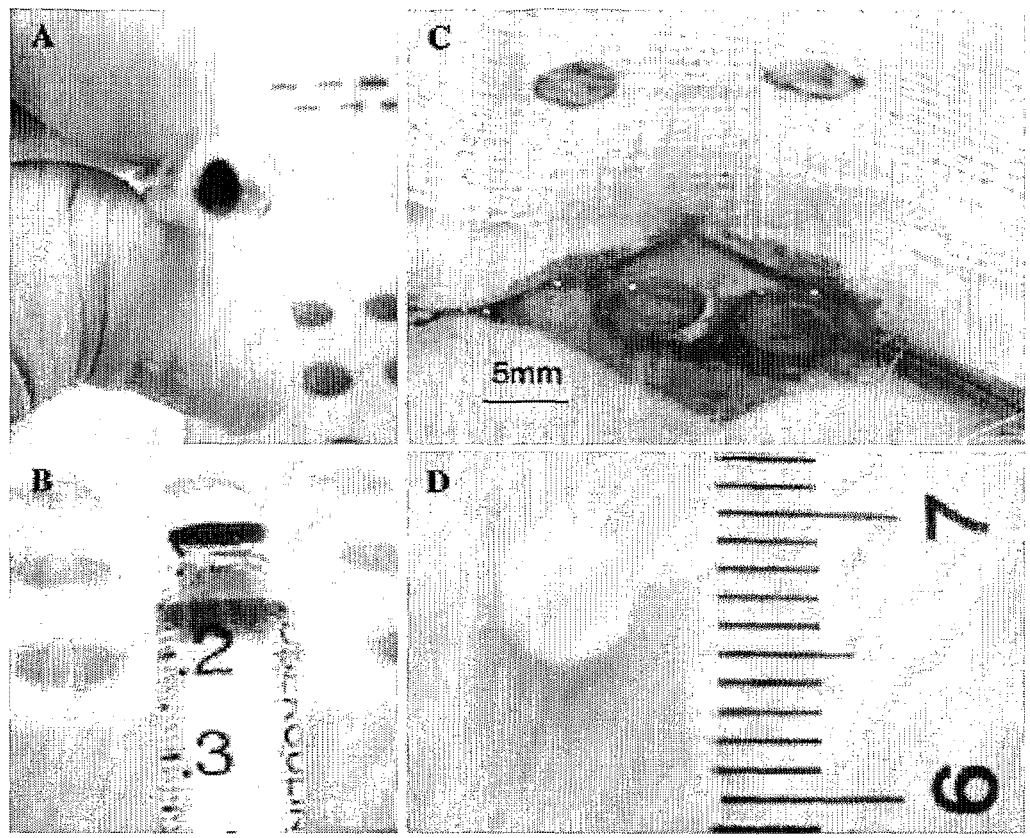
FIG. 1. Fibrin glue scaffold fabrication. Thrombin, fibrinogen and HS-2 were mixed and polymerized in the barrel of a 1 ml modified syringe (A) and ejected after production (B). The sterile fibrin scaffold produced had dimensions of approximately 5 mm in diameter and a thickness of 2 mm (D), which could then be easily implanted directly into the 5 mm defect sites (C).

The details of one or more embodiments of the invention are set forth in the accompanying description below including specific details of the best mode contemplated by the inventors for carrying out the invention, by way of example. It will be apparent to one skilled in the art that the present invention may be practiced without limitation to these specific details.

The present invention concerns the therapeutic role of the neuroepithelium-derived heparan sulfate-2 (HS-2) for the augmentation of bone repair.

Previously heparan sulphate derived from bone (e.g. bone tissue, bone cells or bone precursor cells) has been investigated for use in augmentation of bone repair. The present invention is concerned with an heparan sulphate derived from non-bone sources. In particular, it concerns the use of HS-2 which is derived from embryonic neuroepithelial cells, being neural precursor cells which normally develop into the neural tube before giving rise to immature neurons and neural tissue. The finding that a non-bone, neural tissue derived heparan sulphate is active to improve the regeneration of bone tissue and to improve wound healing in bone in vivo is surprising.

Scaffolds comprising fibrin glue loaded with the embryonic neuroepithelium-derived heparan sulphate-2 were experimentally assessed, firstly in a release-reservoir, and secondly in a scaffold to stimulate bone regeneration in a critical size rat cranial defect.

HS-2 loaded scaffolds are shown to have a uniform distribution of heparan sulfate, which is readily released with a typical burst phase, quickly followed by a prolonged delivery lasting several days. Importantly, the released HS-2 contributes to improved wound healing over a 3 month period as determined by microCT (pCT) scanning, histology, histomorphometry and PCR for osteogenic markers. In all cases, only minimal healing was observed after 1 and 3 months in the absence of HS-2. In contrast, marked healing was observed by 3 months following HS-2 treatment, with nearly full closure of the defect site. PCR analysis showed significant increases in the gene expression of the osteogenic markers Runx2, alkaline phosphatase and osteopontin in the FIS-2 group compared with controls.

The successful delivery of the non-bone derived HS-2 in a hydrogel provides a novel alternative to autologous bone graft and growth factor-based therapies.

Example 1 demonstrates the bone regenerative capability of a single dose of HS-2 encapsulated within a fibrin glue scaffold implanted into a critical sized rat calvarial defect model over a time course of 3 months. The in vitro distribution and the release of HS-2 from the fibrin glue scaffold is described together with the in vivo effects of HS-2 on the process of bone regeneration as determined by microCT (pCT) scanning, histological examination and osteogenic PCR screens.

Example 2 demonstrates the use of a collagen sponge matrix to release HS-2. The Example describes release kinetics and inflammatory response to HS-2 released from a clinically approved collagen sponge.

Example 1

Scaffold Fabrication

Fibrin glue scaffolds were prepared using a commercial kit (TISSEEL kit; Baxter AG). The mould for the cylindrical fibrin glue scaffold was a sterile, modified 1 ml syringe (FIGS. 1A & B) that enabled easy application directly into the defect site once the scaffold had polymerized, so enhancing sterility by eliminating the need to handle any of the scaffolds (FIG. 1C). Fibrinogen (25 µl) was added to 25 µl of thrombin solution, producing a polymerized scaffold of approximately 5 mm diameter and a thickness of 2 mm (FIG. 1D). Two different concentrations of thrombin (Thrombin 4 and Thrombin 500) were investigated in vitro to optimize for the onset of in vivo experiments. The fibrin glue scaffolds created were used as a carrier-matrix for the heparan sulfate delivery as well as to fill up the bone defect site. To incorporate HS-2 into the scaffold, 5 µg HS-2 was added to the thrombin component. This was thoroughly mixed and then pipetted into the sterile modified syringe body before adding the fibrinogen component whilst mixing. The ensuing polymerization of the glue, encapsulating the HS-2, took approximately 1 h. The scaffolds were then examined in vitro for a) HS-2 release, to observe the release kinetics of HS-2 from the fibrin glue, and b) confocal microscopy, to observe the distribution of HS-2 throughout the fibrin glue scaffold, and c) in vivo implantation and µCT evaluation of bone mineralization and histological examination. For the purpose of this study, all in vitro experiments were undertaken using Heparin (Sigma) as a control substitute for HS-2. Heparin is structurally similar to HS, being a hypersulfated variant, and is believed to distribute and release in the same way within a scaffold. It can be easily conjugated to the fluorescent label Alexa Fluor-488, enabling its distribution to be localised and viewed using confocal microscopy, and its release quantified using fluorescent plate reading. All in vivo work utilized HS-2.

Release Kinetics

Fibrin glue scaffolds containing 5 µg Alexa Fluor-488-labelled heparin were placed into 1 ml of pre-warmed phosphate buffered saline (PBS) and incubated at 37° C., protected from light, for a 7 day period. At each time point, 100 µl of PBS was removed for sampling and replaced with fresh PBS. The heparin released was quantified from the fluorescence intensity of the release media at 485 nm by comparison with a standard Alexa Fluor-488-heparin curve. The cumulative release was then graphed.

Confocal Microscopy

Heparin was fluorescently conjugated with Alexa Fluor-488 (A488, Molecular probes) using a method adapted from Osmond (24), prior to incorporation into the scaffold. To visualize the distribution of heparin, scaffolds were viewed using confocal laser scanning microscopy (Zeiss LSM S10 meta inverted microscope). Three dimensional depth projections were constructed from 100 horizontal slices of step size 10 µm.

Surgery

The in vivo study involved the creation of two 5 mm diameter bony defects in the parietal bone. 20 female Wistar rats (300-400 gm) were used with approval from the Institutional Animal Care and Use Committee (IACUC), Singapore. They were randomly divided into 3 groups: (a) defects left empty, (b) defects containing fibrin glue scaffold alone, and (c) defects containing fibrin glue scaffold encapsulating 5 µg HS-2.

Prior to surgery, the rats were given intra-peritoneal anesthesia of 75 mg/kg Ketamine & 1 mg/kg Medetomidine, the heads were shaved and saline-soaked gauze applied across the eyes. Under aseptic technique, the skin over the calvaria was disinfected with Betadine™, the skin over the parietal bone dissected in the sagittal plane and the periosteum removed from the both sides of the parietal bone. A 5 mm diameter trephine was used to create two circular through-and-through, critical-sized bony defects (25) which were irrigated with saline to remove blood clots; proper hemostasis was achieved with gentle pressure. The fibrin glue scaffolds +/−HS-2 were applied directly into the defect sites utilizing the novel syringe system. Then the skin was closed with 5-0 absorbable coated vicryl sutures (polyglactin 910, Johnson and Johnson). The animals were then given reverse anesthetics (5 mg/ml of antisedan), antibiotics and temegesic pain killers. They were placed individually in cages with food and water, and observed postoperatively for any undue adverse effects.

Micro Computed Tomography (µCT) Scanning

At 1 and 3 months after surgery, the rats were anesthetized intra-peritoneally as previously described, before undergoing µCT scanning to obtain a quantitative measure of the levels of regenerated bone (SKYSCAN-1076 in vivo micro computerized tomography scanner, Belgium). Imaging was performed with 68 mm scan width, an Al-1 mm filter, 35 µm pixel size and averaging 4 data into one (26). All the samples were scanned through a 180° rotation angle with a rotation step of 0.8° at 35 µm resolution. The data were volumetrically reconstructed using cone beam CT reconstruction software from SKYSCAN at 1968×1968 pixels. Files were then reconstructed for analysis using Mimics v 8.11 software (Materialize, Belgium) using in-built functions. From the 3D image, a cylindrical region of interest (ROI) of defect size of 5 mm diameter was selected for analysis. This ROI corresponds to the original defect location. The degree of bone regeneration occurring within the defect was presented as a volume in $mm^3$ of reconstructed data obtained in micro CT analysis. The threshold was adjusted empirically to visualize the defect site and the mineralization (−284 to 1420 for all reconstructions). Defect reconstruction was attained by subtracting the scanned mineralization data.

Histology and Histomorphometry

Animals were sacrificed at 3 months in a $CO_2$ chamber. After euthanasia, tissues were dissected from the calvarial bone and the defect site sectioned for histology. Tissues were fixed in 10% neutral buffered formalin for 2 days, and decalcified in 12.5% EDTA (Sigma Aldrich) pH 7.0 for 3 weeks. The samples were serially dehydrated in ethanol in a tissue processor (Shandon Citadel 1000, Thermo Scientific), and paraffin embedded (Leica EG 1160). Sections (5 µm) were taken using a microtome (Leica RM 2135). The slides were deparaffinized with xylene and rehydrated with serial concentrations of ethanol, before being stained with haematoxylin and eosin (Sigma) and mounted with DPX mountant (Fluka Biochemica). Immunohistological staining was also used employing mouse monoclonal antibodies against type I collagen (Sigma) at 1:500 dilution, osteopontin (Santa Cruz) 1:50 dilution, and osteocalcin (Abcam) at 1:150 dilution. Secondary antibodies were rat absorbed anti mouse IgG (Vector). The antigens were localized using an immunoperoxidase procedure according to the manufacturer's guidelines (VECTASTAIN® ABC kit, Vector Labs). A mouse IgG1 negative control was also included (Caltag Laboratories).

Histomorphometry was performed using Bioquant Osteo II software to quantify the percentage staining for collagen I, osteocalcin and osteopontin within the defect site. Briefly, a region of interest was manually drawn around the defect site. The entire defect site was first quantified (total area), and then the percentage of positive stain for each of the aforementioned proteins was quantified and expressed as a percentage of the entire defect site. This positive stain was obtained by manually thresholding the images and directing the software to pick up only the positive stains attributable to the protein of interest (attained through comparisons with negative controls). The thresholds were memorized and applied to every slide within the data set, for each stain.

RNA Isolation and RQ-PCR

Following sacrifice of the animals, the defect sites were surgically collected and immediately frozen using liquid nitrogen. The extracted tissue was then ground to powder form with a mortar and pestle. Total RNA was extracted using Trizol reagent (Invitrogen Corp., USA) and subsequent clean up using an RNeasy Mini Kit (QIAGEN, Singapore) according to the manufacturer's instructions. The quality of the isolated RNA was assessed by gel electrophoresis and quantitated on a Genequant RNA/DNA Spectrophotometer (Amersham Biosciences, Piscataway, N.J., USA) and stored at −80° C. till further use. For conversion to cDNA, 500 ng of total RNA was reverse-transcribed using random hexamers catalysed by Superscript III RT (Invitrogen Corp., USA). Following spectrophometric quantitation of the cDNA, expression levels of the target genes were determined using RQ-PCR. Briefly, 120 ng of cDNA was amplified in triplicate twice using the ABI Prism FAST 7500® sequence detection system (PerkinElmer Life Sciences, Wellesley, Mass., USA) using the default cycle: 95° C.×20 sec followed by 40 cycles of 95° C.×3 sec, 60° C.×30 sec. Runx2, OP and 18S primers and probes were designed using Primer Express software (v 2.1, PE Applied Biosystems, Foster City, Calif., USA), and have been described elsewhere (27). ALP primer probes were purchased as an Assay-on-demand (PE Applied Biosystems, Foster City, Calif., USA). The Runx2 LNA probe was re-designed to incorporate LNA bases and labeled with BHQ-1 (Proligo, Singapore). The ribosomal subunit gene 18S (VIC/TAMRA) was used as the endogenous control. Data was analyzed using the ABI Sequence Detector software. Amplifications were performed three times in triplicate. Target gene expression values ($2^{-\Delta\Delta Ct}$) and were calculated relative to 18S expression levels Statistical Analysis A two-way ANOVA with differences considered significant at the 95% confidence interval, was used to determine significant differences between mineralization within the HS-2 and non-HS-2 treated scaffolds followed by the Bonferroni post-test. Standard error bars were included in all graphs and represent the 95% confidence interval.

In Vitro Analysis of HS-2 Loaded Fibrin Glue Scaffolds

To examine the distribution of heparin through the fibrin scaffold and to assess its time-based release, a combination of confocal microscopy and fluorescent spectroscopy was performed. Confocal microscopy demonstrated an even distribution of heparin (HS-2 substitute) throughout the body of the fibrin scaffold. Sequential scans of 10 µm slices were taken and showed no significant change in heparin distribution between each slice throughout the whole body of the scaffold (data not shown).

Figure 2:
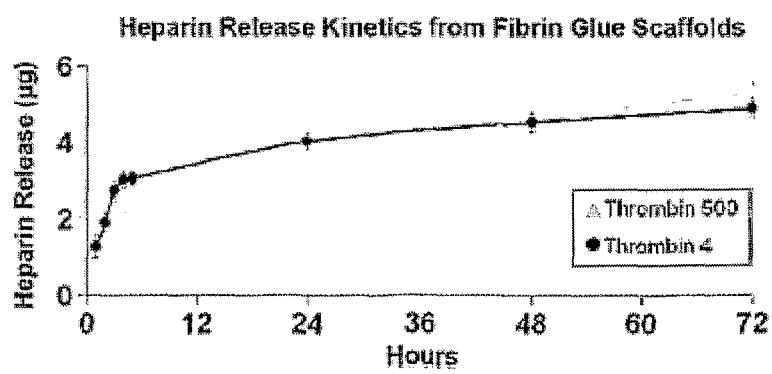
FIG. 2. In vitro analysis of release kinetics of Alexa-468-hepain from fibrin scaffolds revealed a sharp initial burst of over 50% total heparin released in the first 4 h followed by a sustained release of up to 100% over 4 days. ▲=Thrombin 500 ●=Thrombin 4.

FIG. 2 shows the release kinetics of heparin from the scaffold, using both Thrombin 4 and Thrombin 500 components. The release from both scaffolds followed the same pattern; a fast initial burst with over 50% release within the first 4 h, followed by a sustained release over the course of 4 days, at which time 100% of the heparin had been released. Only thrombin 4 was used for in vivo studies after initial trials proved the polymerization rate of Thrombin 500 was too rapid, so prone to air bubbles and uneven encapsulation of the heparin component.

In Vivo Analysis of HS-2 Loaded Fibrin Glue Scaffolds

Figure 3:
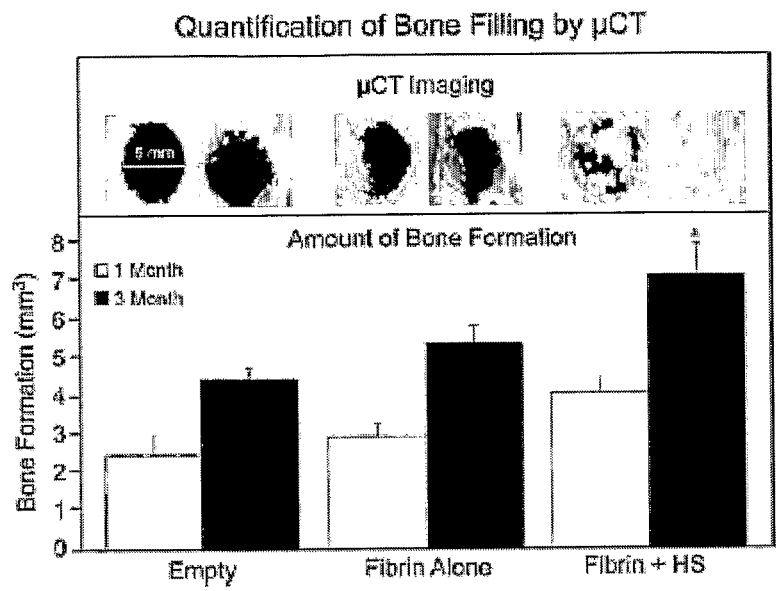
FIG. 3. Quantified μCT of defect sites at 1 and 3 months for empty defect sites, fibrin glue alone and HS treated sites. MIMICs evaluation of the total volume of mineralized bone, in $mm^3$, detected within the defect sites. Asterisk (*) denotes a significant difference between HS treated sites and all other defect sites at 3 months.

The effect of HS-2 on augmenting in vivo bone healing was assessed by pCT and histomorphometry. MicroCT scanning detected significant increases in mineralization for those defect sites treated with HS-2 at both 1 month and 3 months. FIG. 3 depicts representative reconstructions of defect sites at 1 and 3 months for empty defects, fibrin glue alone and HS-2 loaded fibrin glue scaffolds. At 3 months the HS-2 treated sites had full closure of the defect with mineralized bone. The quantitation of this mineralization using MIMICs software showed significantly higher bone present in the HS-2 treated sites at 3 months compared with empty defect sites and fibrin glue alone defect sites (p<0.05). No significant differences were found after only 1 month. All treatments demonstrated significant increases from month 1 to 3 within their respective groups.

Figure 4:
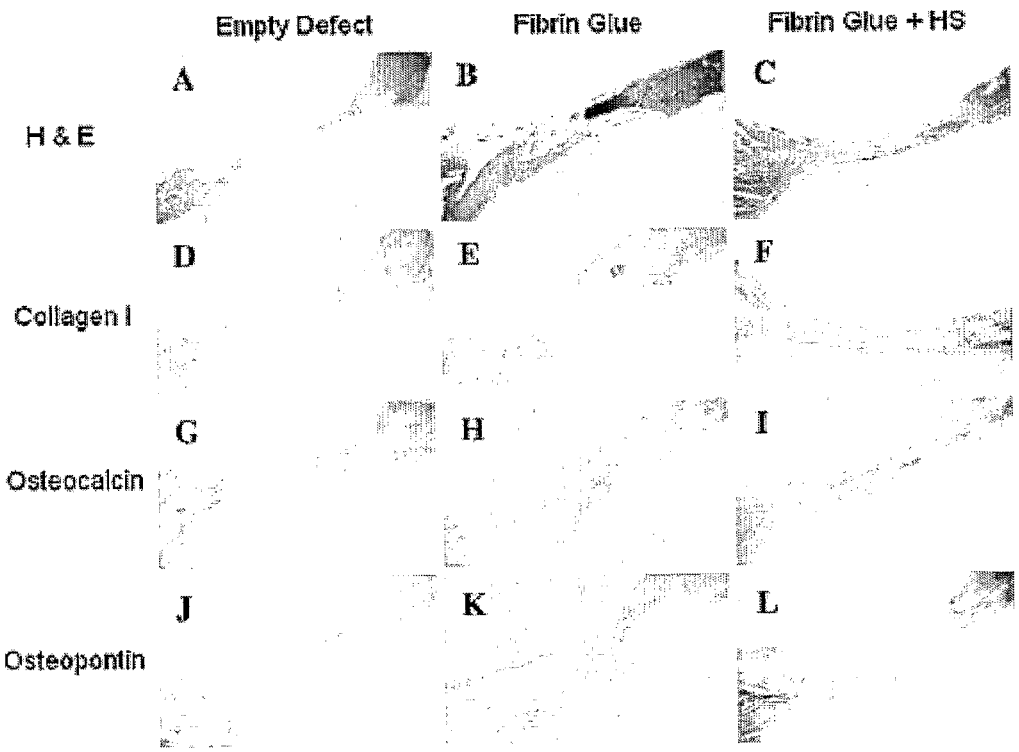
FIG. 4. Representative photographs of tissue section analysis of haemotoxylin and eosin (A-C), and immunohistochemical staining for type I collagen (D-F), osteocalcin (G-I) and osteopontin (J-L) within each defect site after 3 months.
Figure 5:
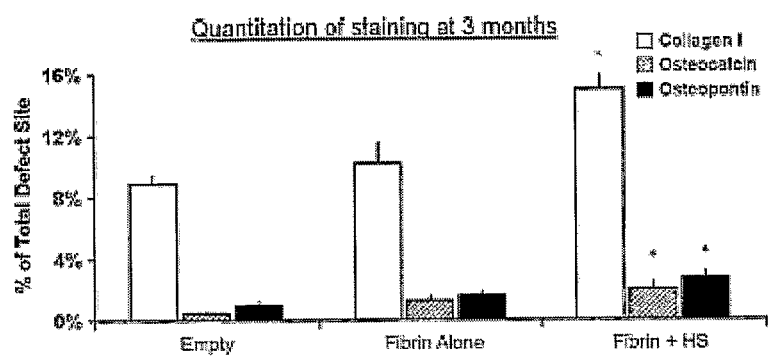
FIG. 5. Quantification of staining as a percentage of total tissue formation after 3 months determined using Bioquant image analysis software. Asterisk (*) denotes a significant difference between HS-2 treated sites and all other sites.

We then examined the isolated and sectioned samples histologically using hematoxylin and eosin (H&E) staining and immunohistochemistry. The fibrin glue alone defect sites appear to have residual bone chips present from surgery, possibly owing to incomplete drilling through the parietal bone, and appear to be composed of newly formed bone with more intense and uniform staining, containing sparse, non-contiguous islands within the defect area (FIG. 4B). The empty defects appear to have only sparse fibrous connective tissue bridging between the bony fronts (FIG. 4A). In the HS-2 treated samples, newly formed, contiguous bone can be observed with and surrounding all edges of the defect site (FIG. 4C). The osteogenic markers collagen type I, osteocalcin and osteopontin all gave demonstrably higher staining within the HS-2 treated groups when compared with empty defects. Collagen I was lowly detectable and disordered in both the empty and fibrin glue defect sites (FIG. 4D, E). In contrast, in the HS-2 treated samples, collagen I had a more organised and fibrillar appearance along the direction of the fibrous tissue, contiguous with the structured bone edges of the defect site (FIG. 4F). Osteocalcin staining was very low in both the empty and fibrin defect sites, with signal detected predominantly in the bone edges of the defect site (FIG. 4G, H). In the HS-2 treated defect sites, osteocalcin staining was uniform throughout both the bone edges and the repaired defect site (FIG. 4J). Osteopontin was very low in the empty defect samples (FIG. 4J) but was present throughout the fibrin-treated defects (FIG. 4K). The distribution of osteopontin throughout the HS-2 treated defects appeared to be mostly localised to the bone edges (FIG. 4L). When we quantified the staining within the defect sites using Bioquant analyses, these observations were reinforced with HS-2 treated defects determined to have significantly higher levels of collagen type I, osteocalcin, and osteopontin at 3 months (FIG. 5).

RQ PCR

To further assess bone formation, a panel of mRNA transcripts (Runx2, ALP and OP) were assessed by RQ PCR. FIG. 5 reveals significant upregulation of Runx2, alkaline phosphatase and osteopontin in HS-2 treated groups compared with fibrin glue alone. Notably, Runx2 underwent a 6-fold upregulation, alkaline phosphatase a 3-fold upregulation and osteopontin a 2-fold upregulation in HS-2 treated samples compared to controls.

Bone is a dynamic and multifunctional organ, capable of remodeling and self-regeneration. However, in extreme cases of non-union or delayed fracture union, therapeutic intervention is often required. In conventional procedures, the transplantation of bone requires invasive procedures such as skin and mucosal incisions and reflection of the periosteum. The ability to implant a bioactive scaffold with osteoinductive properties within a critical sized defect, is an attractive one, especially if the therapy negates the requirement to include live cells in the scaffold.

It has been shown that the local or systemic application of a number of growth factors such as FGF2 and BMP2 (2, 14) can aid bone repair. Disadvantages of such application include their rapid clearance rates and susceptibility to proteolytic degradation (28). Additionally there is concern over their long-term safety, particularly as large quantities are required, with their high associated costs. HS binds to a variety of soluble proteins involved in the control of cell phenotype, including heparin-binding growth factors such as the FGFs, the TGF-βs and the BMPs, increasing their binding to high affinity receptors. HS acts to concentrate growth factors close to cells, protect them from extracellular proteases, shepherd them to the cell surface and facilitate binding to their specific receptors (1). The complexes formed can be readily dissociated and mobilized in the event of tissue damage, resulting in a prolonging of bioactivity at the site of tissue damage (12). Heparan-like mimetics (carboxymethylbezylamide-sulfonated dextrans) have been reported to induce the repair of rat skull defects (15), and single 5 μg doses of HS have been shown to augment fracture repair in a rat fracture model (14). This study sought to investigate the effects of the non-bone cell derived HS-2 on bone regeneration within a critical sized rat cranial defect using fibrin glue as a release reservoir. We utilised μCT scanning to determine bone mineralization within the defect sites and reinforced this with histological and histomorphometrical examination of the defect sites.

MicroCT analysis showed significant bone regeneration within defects treated with HS-2 compared to empty defects and fibrin glue alone, with full closure of some sites after 3 months. This corresponds with studies by Jackson (14) and Blanquaert (15), each of whom demonstrated increased bone regeneration through addition of bone derived HS and HS-like molecules as observed by radiomorphometry and histomorphometry. Our histology showed clear differences in tissue formation among the various treatment sites. Sparse fibrous connective tissue was found to traverse the empty defects, compounded by the lowest levels of staining for collagen I, osteocalcin and osteopontin; significantly lower than HS-2 treated sites at 3 months.

Newly formed bone can be observed surrounding all edges of the defect site in (FIG. 4C) with more intense and uniform staining than that present in the fibrin glue alone defect sites, which seemed only to contain sparse islands within the area of the defect site not contiguous with the bony front (FIG. 4B). Collagen staining was faint and disordered for the empty and fibrin glue alone defect sites (FIGS. 4D&E) but had a more organized fibrillar appearance within the HS-2 treated site along the direction of the fibrous tissue, contiguous with the old structured bone/edges of the defect site (FIG. 4F) The fibrin glue defect site appears to have residual bone chips present from surgery, possibly owing to incomplete drilling through the parietal bone. The quantitation of staining within the defect sites revealed HS-2 treated defects to have significantly higher levels of collagen type I, osteocalcin and osteopontin than either empty defect sites or fibrin glue defect sites after 3 months. Additionally RQ-PCR demonstrated a 6-fold up regulation of Runx2, a 3-fold up regulation of alkaline phosphatase and a 2-fold up regulation of osteopontin in the HS-2 treated groups compared with fibrin glue alone. It should be noted that it was difficult to obtain sufficient tissue from the empty defect sites to enable RNA extraction. Runx2 has been shown to be essential for both skeletal patterning during embryogenesis and the progression of osteoblast differentiation (29-33). Calvarial cells harvested from Runx2-deficient mice have increased rates of cell proliferation, DNA synthesis and G1/S phase markers; the reintroduction of Runx2 restores normal cell cycling, emphasizing the importance of Runx2 for cell cycle regulation (34).

Fibrin glue is a physiologically relevant matrix whose principle component, fibrin, has fundamental roles in the process of blood clotting and wound healing. It is also a potentially suitable biological vehicle for cell transplantation, as it has proven biocompatibility, biodegradability and binding capacity to cells (35). Fibrin stabilizing factor XIII, contained in fibrin glue, favours migration of undifferentiated mesenchymal cells on the highly cross linked structure of the glue and it enhances proliferation of these cells (36, 37). The fibrin glue scaffolds in this study were comprised from a low concentration of thrombin; thrombin 4 (as opposed to thrombin 500) as the workability and incorporation of HS-2 into the polymerizing glue proved difficult using high concentrations; increasing the thrombin concentration has been shown to affect fiber thickness, porosity and homogeneity of the fibrin (38). Heparin (the HS-2 control) was released rapidly in the first 4 h from the fibrin glue, with over 50% total heparin released in the first 4 h followed by a sustained release, up to 100% over 4 days. This sharp burst may have provided the initial stimulus for growth factor recruitment and the onset of bone regeneration. The current study utilized a dose of 5 μg HS-2, encapsulated within a fibrin glue delivery system, within critical sized rat cranial defects. Our results suggest that enhancing growth factor activity within the defect site through the medium of HS-2 sugar, so increasing the expression of osteogenic genes, has significant therapeutic effects upon bone regeneration.

Example 2

Materials and Methods
Collagen Scaffold

Collagen sponges were purchased from Integra Life Sciences (HELISTAT®, Integra Life Sciences Corp, USA) and measured 7×21×5 mm. For all assays, sponges were cut evenly into six pieces measuring 7×7×5 mm and kept sterile. The morphology of the sponges was evaluated using Scanning Electron Microscopy (SEM). Briefly, collagen sponges were sputtered-coated with gold and then examined using SEM (Jeol JSM 5310 LV) at an accelerating voltage of 10 kV.

Fluorescent Labeling of Heparin

For non-biological in vitro assays, heparin, a hypersulfated member of the HS glycosaminoglycan family, was conjugated with Alexa Fluor 488 (A488, Molecular Probes, UK) using a method published previously by our group (39). Briefly, 3 mg of heparin (H-3149) was solubilized in 300 μl of 0.1 M solution of 4-morpholinoethanesulfonic acid (MES, M3671) buffer (pH 4.5) and combined with 50 μl of a 10% 1-ethyl-3-(3-dimethylaminopropryl)carbodiimide hydrochloride (EDC, Fluke 03449) solution in 0.1 M MES buffer. Following, a 1% A488 solution (50 μl) in 0.1 M MES buffer was added to the heparin/EDC solution. The mixture was protected from light and incubated overnight at room temperature. The fluorescently conjugated heparin was eluted on an Amersham PD10, desalting columm. The labeling efficiency was approximately 1.3 mol A488/mol heparin.

Release Profile

Collagen sponges were passively adsorbed with 500, 250, 125, 50, 10 and 0 μg of A488-heparin (50 μl), protected from light, and placed in 1 ml of PBS at 37° C. for 24 h. At 1, 2, 3, 4, 5, 6, and 24 h, 100 μl of conditioned PBS was collected for sampling and replaced with fresh PBS. Additionally, sponges were visualized by fluorescent microscopy at each time point using an Olympus SZX12 stereomicroscope. The concentration of released A488-heparin was quantified by fluorometry and cumulative release of A488-heparin was reported as a percentage of loading concentration.

Pro-Inflammatory Response to HS-2 Pretreated Collagen Sponges

Short-term inflammatory responses to the HS-2/collagen composite was evaluated over 24 h and assessed by measuring endogenous levels of tumor necrosis factor alpha (TNF-α) in the culture media. Mouse RAW264.7 macrophages were seeded ($1.5 \times 10^5$ cells/cm$^2$) in 48-well plates and cultured for 24 h in the presence of HS-2 conditioned media or media containing exogenous HS-2 (160 ng/ml). The amount of (TNF-α) secreted into the media in response to the treatment media was quantified using TNF-α ELISA kit (BD Bioscience, USA) as per the manufacturer's instructions. Cells stimulated with 10 ng/ml lipopolysaccharide (LPS, Fluke, Germany) were used as a positive control, while cells grown in basal media without stimulation provided measurement of background TNF-α levels.

Statistical Analysis

All assays were performed in triplicate, with three independent trials. Results are reported as mean±standard error. Significance ($p<0.05$) was determined by analysis of variance (ANOVA) followed by Tukey-Kramer post hoc analysis.

Figure 6:
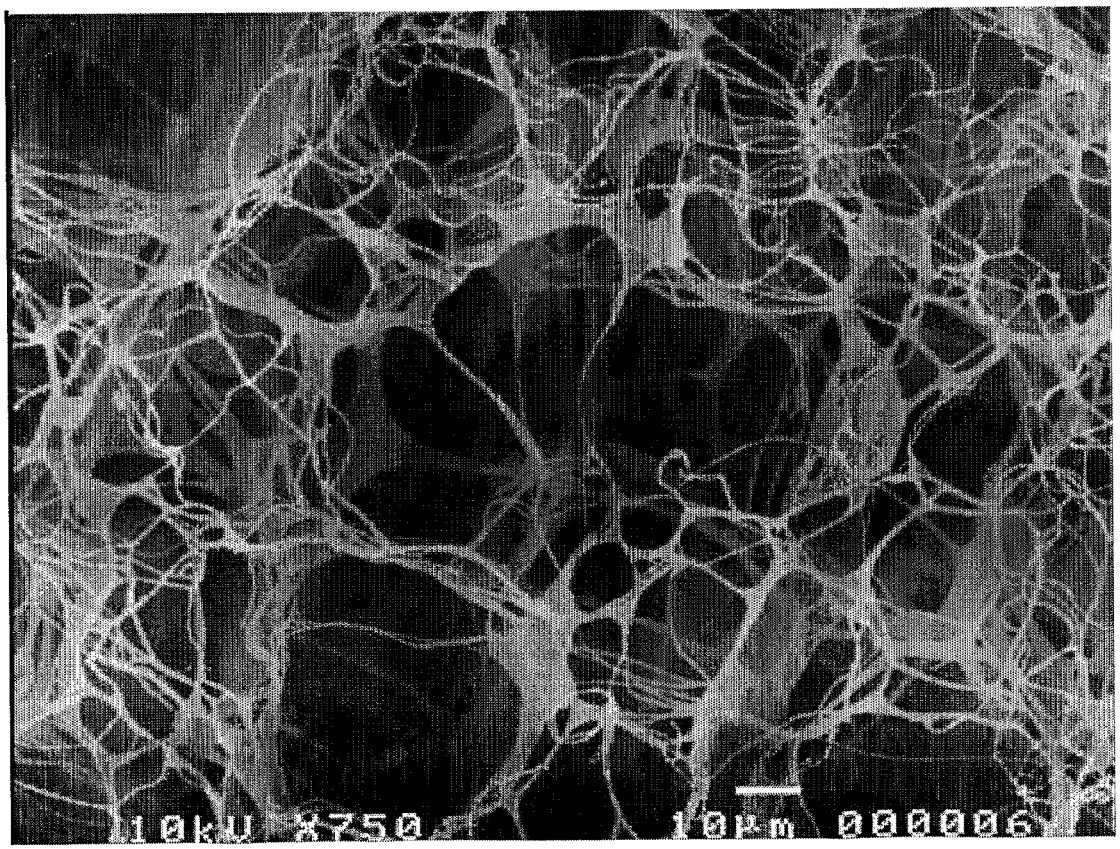
FIG. 6. Morphology of collagen sponge. Sponges were sputtered-coated with gold and then examined using SEM (Jeol JSM 5310 LV) at an accelerating voltage of 10 kV.
Figure 7:
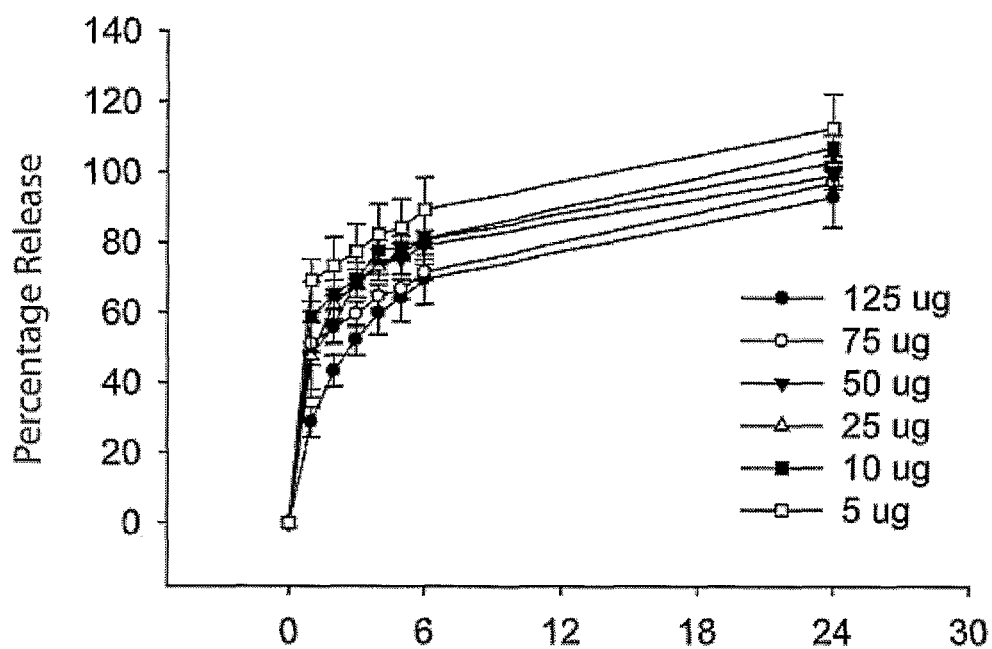
FIG. 7. Heparin releases from collagen sponges within 24 h. Heparin was fluorescently labeled with Alexa-488 and its release from the collagen sponges was quantified by fluorometry over 24 h.

To examine the morphology of the collagen sponges, SEM was performed. As shown in FIG. 6, the sponges have a high porosity (average pore size 20 μm diameter) that contributes to their ability to support nutrient infiltration, the passive adsorption of molecules, and cell colonization. For non-functional assays, we used heparin to mimic HS-2. In order to detect passively adsorbed heparin upon release, we fluorescently conjugated the GAG with an Alexa488 probe for both visualization and quantification by fluormetry. As expected, we found passively absorbed heparin released with an initial burst phase from the collagen sponges, with more than 50% releasing within the first hour and 100% released by 24 h regardless of initial coating concentration (FIG. 7). This was also evidenced visually by qualifying the decrease in fluorescent intensity with time as the treated sponges were immersed in PBS.

Figure 8:
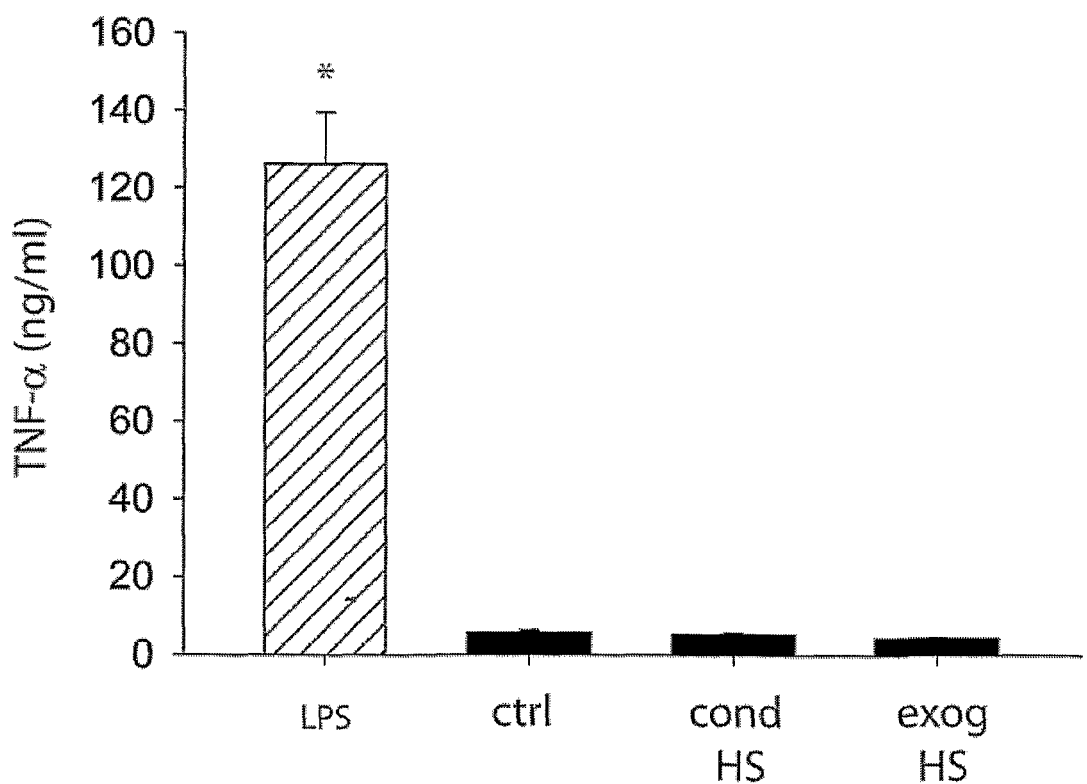
FIG. 8. HS delivered from a collagen sponge does not promote an inflammatory response. Collagen sponges were treated with 160 ng HS and incubated for 24 h to allow 100% release of HS into the media (1 ml). Conditioned media (cond HS) was collected and added onto mouse RAW264.7 macrophages for 24 h. TNF-α levels were assayed using ELISA. Exogenous HS (160 ng/ml) or LPS (10 ng/ml) stimulated macrophages were used as controls. Asterisk (*) indicates a significant difference (p<0.05).

As the structures of heparin and HS-2 are comparable, we assumed the same release kinetics from the collagen sponge as that of passively adsorbed HS-2. Thus it was assumed that 100% of the HS-2 releases from the collagen scaffold by 24 h; this time period was then selected to collect the conditioned media and assay inflammatory responses. We therefore incubated pretreated HS-2 sponges for 24 h in serum-free media to allow 100% of the HS-2 to release. The sponge conditioned media, both with or without HS-2 induced only background levels of TNF-α production, while LPS stimulation gave a significant TNF-α response (FIG. 8). The lack of a pro-inflammatory response induced by the HS-2 treated sponges in vitro indicates this delivery system is suitable for in vivo use.

As expected, passively adsorbed HS-2 released with an initial burst from the collagen sponge, followed by a sustained release of up to 100% by 24 h. Jackson et al. (13) observed that a single, once-off application of bone-derived HS at the time of injury was able to significantly improve bone formation by 20% within the healing callus. Similarly, Example 1 identifies that HS-2, released from fibrin glue with an initial burst phase (50% within the first 4 h), reaching 100% release by 4 days, significantly healed a rat critical size cranial defect compared to that induced by non-treated fibrin glue composites.

Similar to other studies (39), we found that sponges treated both with and without HS-2 only induced background levels of TNF-α indicating their potential use as a biocompatible delivery system of HS-2.

Various substrates including hydrogels (40-42), bone cement (43), collagen (44), and titanium (45), as well as other materials have been derivatized with heparin, a hypersulfated form of HS, in order to provide bioactive and sustained release of such heparin binding growth factors (HBGFs) as VEGFs, FGFs, and BMP-2. These studies demonstrate the potent ability of heparin to protect HBGFs and promote a more effective and efficient release of these factors from the biomaterial carrier. However, using heparin has limitations due to its lack of specificity, its anti-thrombogenic activity, and its plethora of unwanted side effects, with thrombocytopenia and osteoporosis being the most notable (46).

This Example describes the delivery of HS-2 from a clinically approved 3-D collagen scaffold. The results of this study clearly support a rationale for exploiting the use of HS-2 for therapeutic purposes. The quick release of HS-2 maintains bioactivity without inducing an inflammatory response.

REFERENCES

1. Simon M. Cool and Victor Nurcombe. The osteoblast-heparan sulfate axis: Control of the bone cell lineage. *The International Journal of Biochemistry & Cell Biology.* 2005, 37; 9: 1739-1745
2. Fakhry, A., et al., 2005. Effects of FGF-2/-9 in calvarial bone cell cultures: differentiation stage-dependent mitogenic effect, inverse regulation of BMP-2 and noggin, and enhancement of osteogenic potential. Bone 36, 254-266.
3. Ornitz, D. M., Marie, P. J., 2002. FGF signaling pathways in endochondral and intramembranous bone development and human genetic disease. Genes Dev. 16, 1446-1465.
4. Zhang, X., Sobue, T., Hurley, M. M., 2002. FGF-2 increases colony formation, PTH receptor, and IGF-1 mRNA in mouse marrow stromal cells. Biochem. Biophys. Res. Commun. 290, 526-531.
5. Rebecca A. Jackson, Victor Nurcombe and Simon M. Cool. Coordinated fibroblast growth factor and heparan sulfate regulation of Osteogenesis. *Gene.* 2006. 379:79-91
6. Guido David and Merton Bernfield. The emerging roles of cell surface heparan sulfate proteoglycans *Matrix Biology.* 1998. 17; 7: 461-463
7. Jeremy Turnbull, Andrew Powell and Scott Guimond Heparan sulfate: decoding a dynamic multifunctional cell regulator. *Trends in Cell Biology* 2001. 11; 2:75-82
8. Malcolm Lyon and John T. Gallagher. Bio-specific sequences and domains in heparan sulfate and the regulation of cell growth and adhesion. *Matrix Biolog.* 1998. 17:7: 485-493
9. Olli Saksela and Daniela Rifkin Release of basic fibroblast growth factor-heparan sulfate complexes from endothelial cells by plasminogen activator-mediated proteolytic activity *Fibrinolysis.* 1989. 3: 36
10. Irie A, Habuchi H, Kimata K, Sanai Y. Heparan sulfate is required for bone morphogenetic protein-7 signaling. Biochem Biophys Res Commun 2003; 308:858-65.
11. Takada T, Katagiri T, Ifuku M, Morimura N, Kobayashi M, Hasegawa K, et al. Sulfated polysaccharides enhance the biological activities of bone morphogenetic proteins. J Biol Chem 2003; 278:43229-35.
12. Coombe D R, Kett W C. Heparan sulfate-protein interactions: therapeutic potential through structure-function insights. Cell Mol Life Sci 2005; 62:410-24
13. Jackson R A, McDonald M M, Nurcombe V, Little D G, Cool S M. The use of heparan sulfate to augment fracture repair in a rat fracture model. J Orthop Res 2006; 24:636-44.
14. Blanquaert F, Saffar J L, Colombier M L, Carpentier G, Barritault D, Caruelle J P. Heparan-like molecules induce the repair of skull defects. Bone 1995; 17:499-506.
15. Lafont J, Blanquaert F, Colombier M L, Barritault D, Carueelle J P, Saffar J L. Kinetic study of early regenerative effects of RGTA11, a heparan sulfate mimetic, in rat craniotomy defects. Calcif Tissue Int 2004; 75:517-25.
16. Emma Luong-Van, Lisbeth Greindahl, Victor Nurcombe Simon Cool. In vitro biocompatibility and bioactivity of microencapsulated heparan sulfate. Biomaterials 2007. 28: 2127-2136
17. Shireman P K, Greisler H P, Fibrin Sealant in vascular surgery: a review. Journal of Long term effects of Medical Implants. 1998; 8: 117-132
18. Weisel J W, Fibrinogen and Fibrin. Advanced Protein Chemistry. 2005; 70: 247-299
19. Rajesh Vasita, Dhirendra S Katti. Growth factor delivery systems for tissue engineering: a materials perspective. Expert Reviews in Medical Devices. 2006; 3(1): 29-47.
20. Wong C, Inman E, Spaethe R, Helgerson S. Thromb. Haemost. 2003 89(3): 573-582
21. Pandit A S, Wilson D J, Feldman D S. Fibrin scaffold as an effective vehicle for the delivery of acidic growth factor (FGF-1). J. Biomaterials Applications. 2000; 14(3); 229-242.
22. DeBlois Cote M F. Doillon C J. Heparin-fibroblast growth factor fibrin complex: in vitro and in vivo applications to collagen based materials. Biomaterials. 1994; 15 (9): 665-672.
23. B Rai, S H Teoh, D W Hutmacher, T Cao, K H Ho. Novel PCL-based honeycomb scaffolds as drug delivery systems for rhBMP-2. Biomaterials 2005; 26: 3739-3748.
24. Osmond R I, Kett W C, Skett S E, Coombe D R. Protein-heparin interactions measured by BIAcore 2000 are affected by the method of heparin immobilization. Anal Biochem 2002; 310:199-207.
25. Catherine. M Cowan, Yun-Ying. Shi, Oliver O, Aalami, Yu-Fen Chou, Carina Mari, Romy Thomas, Natalina Quarto, Christopher H Contag, Benjamin Wu & Michael T Longaker Adipose-derived adult stromal cells heal critical-size mouse calvarial defects; *Nature Biotechnology* 2004 22, 560-567
26. Shao X X, Hutmacher D W, Ho S T, Goh J C, Lee E H. Evaluation of a hybrid scaffold/cell construct in repair of high-load-bearing osteochondral defects in rabbits. Biomaterials 2006; 27(7):1071-80.
27. Kee Woei Ng, Tobias Spiecher, Christian Dombrowski, Torben Helledie, Larisa M Haupt, Victor Nurcombe and Simon M Cool. Osteogenic Differentiation of Murine Embryonic Stem Cells Is Mediated by Fibroblast Growth Factor Receptors. Stem Cells and Development (2007) 16:305-318
28. Babensee J E, McIntyre L V, Mikos A G. Growth factor delivery for tissue engineering. Pharm Res. 2000; 17: 497-504.
29. Ducy P, Starbuck M, Priemel M, Shen J, Pinero G, Geoffroy V, Amling M, Karsenty G. 1999. A Cbfa 1-dependent genetic pathway controls bone formation beyond embryonic development. Genes Dev 13(8):1025-1036.
30. Komori T, Yagi H, Nomura S, Yamaguchi A, Sasaki K, Deguchi K, Shimizu Y, Bronson R T, Gao Y H, lnada M, Sato M, Okamoto R, Kitamura Y, Yoshiki S, Kishimoto T. 1997. Targeted disruption of Cbfa1 results in a complete lack of bone formation owing to maturational arrest of osteoblasts. Cell 89(5):755-764.
31. Mundlos S, Otto F, Mundlos C, Mulliken J B, Aylsworth A S, Albright S, Lindhout D, Cole W G, Henn W, Knoll J H, Owen M J, Mertelsmann R, Zabel B U, Olsen B R. 1997. Mutations involving the transcription factor CBFA1 cause cleidocranial dysplasia. Cell 89(5):773-779.
32. Otto F, Thornell A P, Crompton T, Denzel A, Gilmour K C, Rosewell I R, Stamp G W, Beddington R S, Mundlos S, Olsen B R, Selby P B, Owen M J. 1997. Cbfa1, a candidate gene for cleidocranial dysplasia syndrome, is essential for osteoblast differentiation and bone development. Cell 89(5):765-771.
33. Choi K Y, Kim H J, Lee M H, Kwon T G, Nah H D, Furuichi T, Komori T, Nam S H, Kim Y J, Kim H J, Ryoo H M. 2005. Runx2 regulates FGF2-induced Bmp2 expression during cranial bone development. Dev Dyn 233(1): 115-121.
34. Pratap J, Galindo M, Zaidi S K, Vradii D, Bhat B M, Robinson J A, Choi J Y, Komori T, Stein J L, Lian J B, Stein G S, van Wijnen A J. 2003. Cell growth regulatory role of Runx2 during proliferative expansion of preosteoblasts. Cancer Res 63(17):5357-5362.
35. Keller J, Anderasses T T, Joyce F. Fixation of osteochondral fractures: fibrin sealant tested in dogs. Acta Orthop Scand 1985; 56:323-326.
36. Kasai S. Kunimoto T, Nitta K. Cross linking of fibrin by activated factor XIII stimulates attachment, morphological changes and proliferation of fibroblasts. Biomed Res. 1983: 4: 155-160
37. Marktl W, Rudas B. The effect of factor XIII on wound granulation in the rat. Thromb Diath Haemorrh 1974: 32. 578-581.
38. Damien Le Nihouannen, Laurent Le Guehennen, Thierry Rouillon, Paul Pilet, Melitta Bilban, Pierre Layrolle, Guy Daculsi. Micro-architecture of calcium phosphate granules and fibrin glue composites for bone tissue engineering. Biomaterials 2006: 27:2716-2722.
39. Luong-Van E, Grondahl L, Nurcombe V, Cool S. In vitro biocompatibility and bioactivity of microencapsulated heparan sulfate. Biomaterials. 2007 April; 28(12):2127-36.
40. Cai S, Liu Y, Zheng Shu X, Prestwich G D. Injectable glycosaminoglycan hydrogels for controlled release of human basic fibroblast growth factor. Biomaterials. 2005 October; 26(30):6054-67.
41. Liu Y, Cai S, Shu X Z, Shelby J, Prestwich G D. Release of basic fibroblast growth factor from a crosslinked glycosaminoglycan hydrogel promotes wound healing. Wound Repair Regen. 2007 March-April; 15(2):245-51.
42. Pike D B, Cai S, Pomraning K R, Firpo M A, Fisher R J, Shu X Z, et al. Heparin-regulated release of growth factors in vitro and angiogenic response in vivo to implanted hyaluronan hydrogels containing VEGF and bFGF. Biomaterials. 2006 October; 27(30):5242-51.
43. Lode A, Reinstorf A, Bernhardt A, Wolf-Brandstetter C, Konig U, Gelinsky M. Heparin modification of calcium phosphate bone cements for VEGF functionalization. J Biomed Mater Res A. 2007 Nov. 27.
44. Steffens G C, Yao C, Prevel P, Markowicz M, Schenck P, Noah E M, et al. Modulation of angiogenic potential of collagen matrices by covalent incorporation of heparin and loading with vascular endothelial growth factor. Tissue Eng. 2004 September-October; 10(9-10): 1502-9.
45. Wolf-Brandstetter C, Lode A, Hanke T, Scharnweber D, Worch H. Influence of modified extracellular matrices on TI6AL4V implants on binding and release of VEGF. J Biomed Mater Res A. 2006 Dec. 15; 79(4):882-94.
46. Kock H J, Handschin A E. Osteoblast growth inhibition by unfractionated heparin and by low molecular weight heparins: an in-vitro investigation. Clin Appl Thromb Hemost. 2002 July;8(3):251-5.

The invention claimed is:

1. A method of treating a bone fracture in a human subject, the method comprising administering a therapeutically effective amount of heparan sulfate directly to a fracture site of said subject to treat said bone fracture, wherein the heparan sulfate is HS-2 obtainable from embryonic neuroepithelium and wherein following digestion with heparin lyases I, II and III, the HS-2 has a disaccharide composition comprising:

Disaccharide Percentage
ΔHexUA-GlcNAc 44.8±5%
ΔHexUA-GlcNSO$_3$ 21.5±5%
ΔHexUA-GlcNAc(6S) 8.0±5%
ΔHexUA(2S)-GlcNAc 2.4±5%
ΔHexUA-GlcNSO$_3$(6S) 4.0±5%
ΔHexUA(2S)-GlcNSO$_3$ 12.4±5%
ΔHexUA(2S)-GlcNAc(6S) 0.2±5%
ΔHexUA(2S)-GlcNSO$_3$(6S) 4.1±5%
Unknown 2.4±5% and wherein the method results in an increase in in vivo bone formation as compared to in the absence of the heparan sulphate.

2. The method of claim 1 wherein the method comprises administering the heparan sulfate to the tissue surrounding the fracture.

3. The method of claim 1 wherein administration of the heparan sulfate comprises injection of the heparan sulfate to the tissue surrounding the fracture.

4. The method of claim 1 wherein the heparan sulfate is formulated as a pharmaceutical composition comprising heparan sulfate and a pharmaceutically acceptable carrier, adjuvant or diluent.

5. A method of treating bone fracture in a human subject, the method comprising surgically implanting a biocompatible implant or prosthesis, which implant or prosthesis comprises a biomaterial and a therapeutic amount of heparan sulfate, into tissue of the subject at or surrounding the site of fracture, to treat said bone fracture, wherein the heparan sulfate is HS-2-obtainable from embryonic neuroepithelium and wherein following digestion with heparin lyases I, II, and III, the HS-2 has a disaccharide composition comprising:

Disaccharide Percentage
ΔHexUA-GlcNAc 44.8±5%
ΔHexUA-GlcNSO$_3$ 21.5±5%
ΔHexUA-GlcNAc(6S) 8.0±5%
ΔHexUA(2S)-GlcNAc 2.4±5%
ΔHexUA-GlcNSO$_3$(6S) 4.0±5%
ΔHexUA(2S)-GlcNSO$_3$ 12.4±5%
ΔHexUA(2S)-GlcNAc(6S) 0.2±5%
ΔHexUA(2S)-GlcNSO$_3$(6S) 4.1±5%
Unknown 2.4±5% and wherein the method results in an increase in in vivo bone formation as compared to in the absence of the heparan sulphate.

6. The method of claim 5 wherein the implant or prosthesis is coated with the heparan sulfate.

7. The method of claim 5 wherein the implant or prosthesis is impregnated with the heparan sulfate.

* * * * *